US 7,170,972 B2

Jan. 30, 2007

(12) United States Patent
Altman

(10) Patent No.: US 7,170,972 B2
(45) Date of Patent: Jan. 30, 2007

(54) METHODS AND SYSTEMS FOR MULTI-MODALITY IMAGING

(75) Inventor: Hernan Altman, Nesher (IL)

(73) Assignee: General Electric Company, Schenectady, NY (US)

(*) Notice: Subject to any disclaimer, the term of this patent is extended or adjusted under 35 U.S.C. 154(b) by 0 days.

(21) Appl. No.: 10/801,918

(22) Filed: Mar. 16, 2004

(65) Prior Publication Data
US 2005/0207526 A1 Sep. 22, 2005

(51) Int. Cl.
G01N 23/04 (2006.01)

(52) U.S. Cl. .......................... 378/62; 378/197
(58) Field of Classification Search ............. 378/20, 378/5, 8, 16, 95, 63, 4, 19, 62, 98.8, 193, 378/195, 197; 250/370.12, 363.04, 370.08, 250/380.09
See application file for complete search history.

(56) References Cited

U.S. PATENT DOCUMENTS

| | | | |
|---|---|---|---|
| 6,052,433 A * | 4/2000 | Chao ..................... 378/98.9 |
| 6,147,352 A * | 11/2000 | Ashburn ................ 250/363.05 |
| 6,180,943 B1 | 1/2001 | Lange |
| 6,252,924 B1 | 6/2001 | Davantes et al. |
| 6,256,368 B1 * | 7/2001 | Hsieh et al. ................ 378/8 |
| 6,303,935 B1 | 10/2001 | Engdahl et al. |
| 6,324,247 B1 * | 11/2001 | Besson ..................... 378/15 |
| 6,364,526 B2 * | 4/2002 | Ivan et al. ................ 378/198 |
| 6,368,285 B1 | 4/2002 | Osadchy et al. |
| 6,373,060 B1 * | 4/2002 | Yamakawa et al. ..... 250/363.08 |
| 6,399,951 B1 | 6/2002 | Paulus et al. |
| 6,466,638 B1 * | 10/2002 | Silver et al. ................. 378/4 |
| 6,504,892 B1 | 1/2003 | Ning |
| 6,504,893 B1 * | 1/2003 | Flohr et al. ................ 378/8 |
| 6,631,285 B2 * | 10/2003 | Natterer et al. ........... 600/436 |
| 6,659,642 B2 | 12/2003 | Hanover |
| 6,670,614 B1 | 12/2003 | Plut et al. |
| 6,708,052 B1 * | 3/2004 | Mao et al. ............... 600/407 |
| 6,865,254 B2 * | 3/2005 | Nafstadius ................ 378/65 |
| 7,016,457 B1 * | 3/2006 | Senzig et al. ............. 378/19 |
| 2002/0090050 A1 * | 7/2002 | Nutt et al. ................ 378/19 |
| 2002/0090058 A1 | 7/2002 | Yasuda et al. |
| 2002/0191734 A1 * | 12/2002 | Kojima et al. ............. 378/4 |
| 2003/0128801 A1 * | 7/2003 | Eisenberg et al. .......... 378/19 |
| 2003/0169847 A1 * | 9/2003 | Karellas et al. .......... 378/98.3 |
| 2004/0081277 A1 * | 4/2004 | Amemiya et al. ......... 378/63 |

* cited by examiner

Primary Examiner—Courtney Thomas
(74) Attorney, Agent, or Firm—Evan R. Sotiriou; The Small Patent Law Group

(57) ABSTRACT

A method of examining a patient is provided. The method includes aligning a patient table in an opening of a gantry unit that includes a CZT photon detector and an x-ray source, imaging a patient utilizing a first imaging modality during a first portion of a scan using the CZT detector, and imaging a patient utilizing a second imaging modality during a second portion of the scan using the CZT detector wherein the second imaging modality is different than the first imaging modality.

27 Claims, 3 Drawing Sheets

300 ⮕

302
Aligning a Patient Table in an Opening of an Opening of a C-ARM Unit that Includes a CZT Photon Detector Positioned at a First End of the C-ARM and an X-RAY Source Positioned at a Second Opposing End of the C-ARM

304
Imaging a Patient Utilizing a First Imaging Modality During a First Portion of a Scan

306
Imaging a Patient Utilizing a Second Imaging Modality During a Second Portion of the Scan

*FIG. 3*

METHODS AND SYSTEMS FOR MULTI-MODALITY IMAGING

BACKGROUND OF THE INVENTION

This invention relates generally to imaging systems capable of operation in multiple modalities, and more particularly to methods and systems for performing a volume computer tomography (CT) scan in a multi-modality system.

Multi-modality imaging systems are capable of scanning using different modalities, such as, for example, Positron Emission Tomography (PET), Single Positron emission tomography (SPECT), Computed Tomography (CT), Static X-Ray imaging, and Dynamic (Fluoroscopy) X-Ray imaging. In a multi-modal system (also referred to as a multi-modality system), a portion of the same hardware is utilized to perform different scans (e.g., an image produced by SPECT is processed and displayed respectively, by the same computer and display, as an image produced by CT). However, the data acquisition systems (also referred to as an "imaging assembly") are different. For example, on a CT/SPECT system, a radiation source and a radiation detector are used in combination to acquire CT data, while a radiopharmaceutical is typically employed in combination with a SPECT camera to acquire SPECT data.

CT imaging is typically performed using an x-ray source that is collimated into a relatively thin fan-beam of x-rays that radiate from the x-ray source towards a detector. A CT detector is typically a thin linear detector positioned to receive the fan-beam of x-rays radiated by the x-ray source. However, nuclear medicine imaging, such as, but not limited to SPECT imaging is performed using a volume detector wherein a length dimension and a width dimension may be relatively similar. However, even a detector that is capable of imaging both x-ray transmission and gamma ray emission, for example, a CZT detector with a count mode and a high count rate capability, would only use a portion of the CZT detector during a CT portion of a scan.

BRIEF DESCRIPTION OF THE INVENTION

In one embodiment, a method of examining a patient is provided. The method includes aligning a patient table in an opening of a gantry unit that includes a CZT photon detector and an x-ray source, imaging a patient utilizing a first imaging modality during a first portion of a scan using the CZT detector, and imaging a patient utilizing a second imaging modality during a second portion of the scan using the CZT detector wherein the second imaging modality is different than the first imaging modality.

In another embodiment, an imaging system is provided. The imaging system includes a gantry unit having an x-ray source for generating x-rays and a CZT detector configured to detect emission gamma photons and transmission x-ray photons, the gantry moving the x-ray source and detector along an image acquisition path between at least first and second imaging positions.

BRIEF DESCRIPTION OF THE DRAWINGS

FIG. 3 is a flowchart of an exemplary method that may be used to perform a multi-modality image scan of an object using the imaging system shown in FIG. 1.

DETAILED DESCRIPTION OF THE INVENTION

Although the present invention is described in the context of a an exemplary C-arm gantry, it should be understood that any configuration of gantry capable of performing the functions described herein is contemplated as being used.

Figure 1:
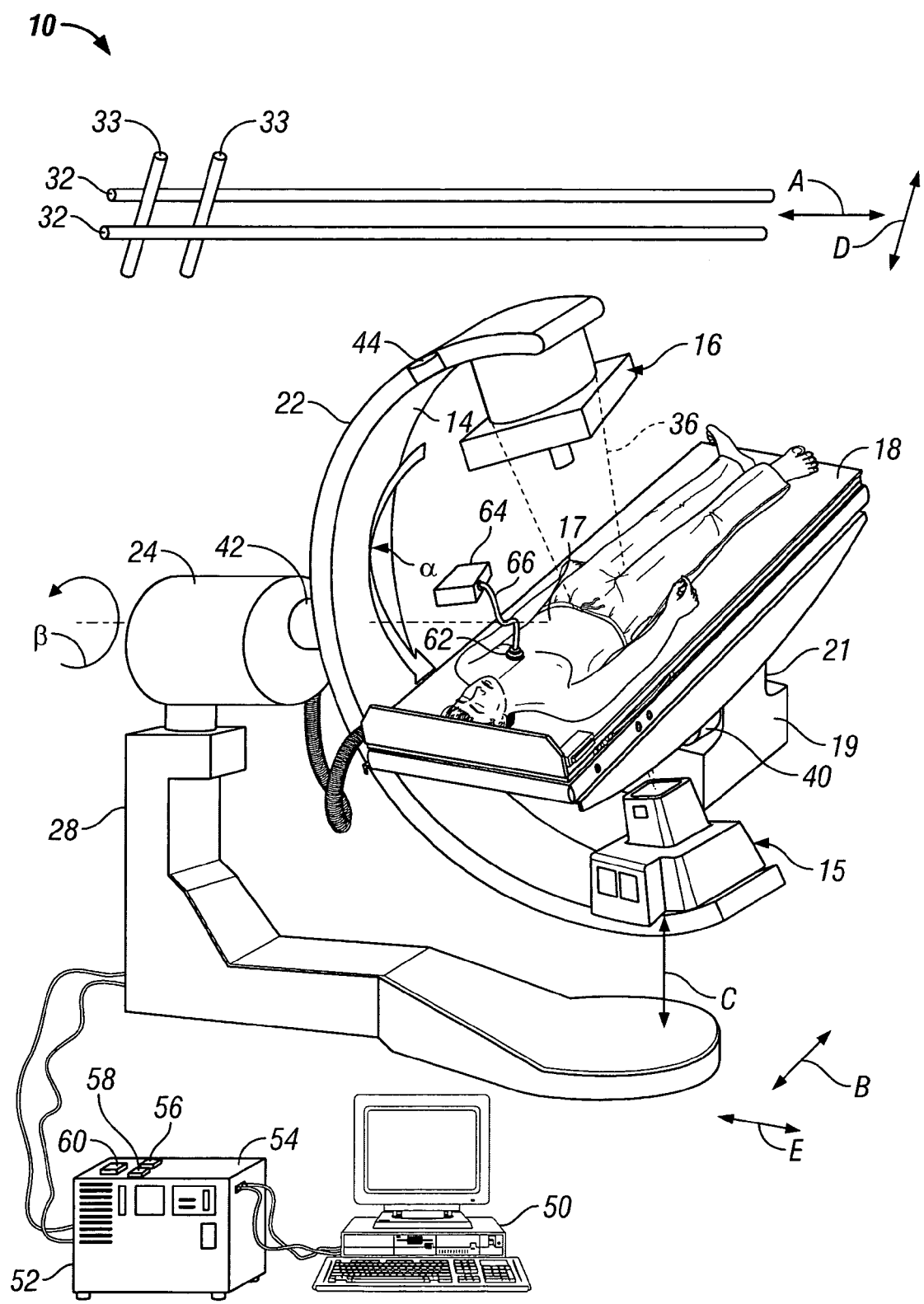
FIG. 1 is a schematic illustration of an imaging system in accordance with an exemplary embodiment of the present invention.

FIG. 1 is a schematic illustration of an imaging system 10 in accordance with an exemplary embodiment of the present invention. An X-ray source 15 and a dual x-ray/gamma ray detector 16 are attached to the two ends of a C-arm 14. X-ray source 15 generates X-rays when applied with a high voltage (e.g., 10,000 volts) from a high voltage generator (not shown). In the exemplary embodiment, x-ray source 15 generates a cone-beam of x-ray photons that are projected from x-ray source 15 towards dual x-ray/gamma ray detector 16 in a diverging conical projection at a predetermined fan angle. In an alternative embodiment, x-ray source 15 generates a fan beam of x-ray photons. Dual x-ray/gamma ray detector 16 may be fabricated of a flat panel Cadmium Zinc Telluride (CZT) semiconductor. A photoconduction process within the CZT semiconductor generates electron-hole pairs in an interaction with X-rays and/or gamma photons. The electron-hole pairs move to respective electrodes to be output as an electrical signal comprising photon count and energy data.

In imaging an object 17, such as, a patient, object 17 is placed on a patient table top 18 of a bed 19 and is positioned between X-ray tube 15 and dual x-ray/gamma ray detector 16. Object 17 may include a radiopharmaceutical that concentrates in a predetermined region of object 17 and emits emission gamma rays (not shown in FIG. 1). As C-arm 14 rotates, object 17 may be imaged with x-rays over a predetermined arc such that a plurality of image views are received, while object 17 remains positioned substantially directly between x-ray emitting source 15 and dual x-ray/gamma ray detector 16. A field of view of imaging system 10 may be established by a width of dual x-ray/gamma ray detector 16 in a plane of rotation. Dual x-ray/gamma ray detector 16 may be translated in this plane to facilitate increasing an effective field of view of imaging system 10 during the rotation. Dual x-ray/gamma ray detector 16 may be included in a plurality of imaging assembly modalities and/or multi-modality imaging assemblies, for example, any combination of a SPECT imaging assembly, a PET imaging assembly, a CT imaging assembly, a Static x-ray imaging assembly, and a Dynamic (Fluoroscopy) x-ray imaging assembly. Bed 19 has a table top slide/ascent and descent mechanism 21 for sliding table top 18 in a forward and a backward direction B, in a sideways direction E, and in a vertically ascending and a descending direction C.

To be able to freely change the imaging direction of object 17, C-arm 14 is slidably rotatable in a direction α (alpha) along a circumference of C-arm 14 using a C-arm holder 22, and is rotatable in a direction β (beta) using a holder base 24. The axes of rotation of directions α and β are substantially perpendicular to each other.

Holder base 24 may be coupled to a suitable support structure (not shown), such as, a wall, a floor, and/or a ceiling, through a support base 28. Support base 28 may be supported to allow for slidable operation along arrows A and D using two systems of rails 32 and 33 coupled to the ceiling, the floor, or cantilevered from the wall. Rails 32 and 33 may be perpendicular with respect to each other. By combining the slides in the directions of arrows A and D and the slides, ascent, and descent in the directions of the arrows B, C, and E of table top 18, the position of object 17 may be changed.

Imaging system 10 uses a volume CT scanning portion to examine object 17 (e.g. a human patient, an animal patient, or an inanimate object) using a cone shaped radiation beam 36 which traverses a set of paths across object 17. X-ray source 15 and dual x-ray/gamma ray detector 16 are mounted on C-arm 14 that rotates around object 17 being examined. In the exemplary embodiment, an operating voltage for x-ray source 15 is obtained from a conventional high-voltage generator (not shown) in such a manner that x-ray source 15 generates cone-shaped beam 36 of x-ray radiation when high-voltage is applied to it. In an alternative embodiment, a x-ray opaque shutter (not shown) is used to substantially block an emission of x-rays from x-ray source 15, for example, when x-ray source 15 is used in a continuous on mode while still modulating the emission of x-rays.

Cone-shaped beam 36 of radiation generated by x-ray source 15 is projected through object 17 being scanned. Dual x-ray/gamma ray detector 16 measures the x-ray radiation transmitted along paths across cone-shaped beam 36.

C-arm 14 may be rotated in direction $\alpha$ and/or $\beta$ to cause x-ray source 15 and dual x-ray/gamma ray detector 16 to rotate around object 17 while images are being taken, both in a transmission x-ray portion of a scan and an emission gamma portion of a scan. Rotation, tilting, and relative linear motion between dual x-ray/gamma ray detector 16 and object 17 permits any desired data acquisition geometry, including, for example, a circle, a circle plus arc, and a circle plus line, a circle plus multiple lines, a circle plus multiple arcs, a spiral, and a 180 degree plus fan width geometry.

A sensor 40 coupled to bed 19 detects a position of patient table top 18 with respect to bed 19 in each direction B, C, and E. A sensor 42, which may include a rotary encoder detects rotational direction $\beta$ and a sensor 44, which may include a linear encoder, detects C-arm 14 travel along axis $\alpha$ of C-arm holder 22. An output of each sensor may be transmitted to a processor 50 through a control interface 52. Processor 50 may generate control signals for controlling the position of bed 19 and C-arm 14 during a scan based on the sensor outputs, based upon for example, user inputs or a predetermined scan.

During a scan, in the exemplary embodiment, volume data from a CT portion of a scan and from a SPECT portion of a scan is transmitted from dual x-ray/gamma ray detector 16 to processor 50 through a data interface 54. Data interface 54 may include a transmission photon signal electronics circuit, such as a processor 56 having a count mode and a high count rate capability for processing transmission image data. Data interface 54 may also include an emission photon signal electronics circuit, such as processor 58, for processing emission image data, and a switch 60 for selecting between processors 56 and 58.

For example, when operating in a cardiac gating mode, the CT portion of the scan and/or the SPECT portion of the scan may be gated from a signal relative to a functioning of a heart 62 within object 17. A heart monitor 64 may be connected to object 17 through a conduit 66 to generate an output signal, which may be used to modulate x-ray source 15 to synchronize transmission and/or emission image acquisition with a cardiac cycle of heart 62. In the exemplary embodiment, heart monitor 64 controls high voltage to x-ray source 15 to reduce a x-ray output of x-ray source 15 relative to the functioning of heart 62. In an alternative embodiment, heart monitor 64 controls a position of a x-ray opaque shutter to reduce the x-ray output of x-ray source 15 relative to the functioning of heart 62.

Figure 2:
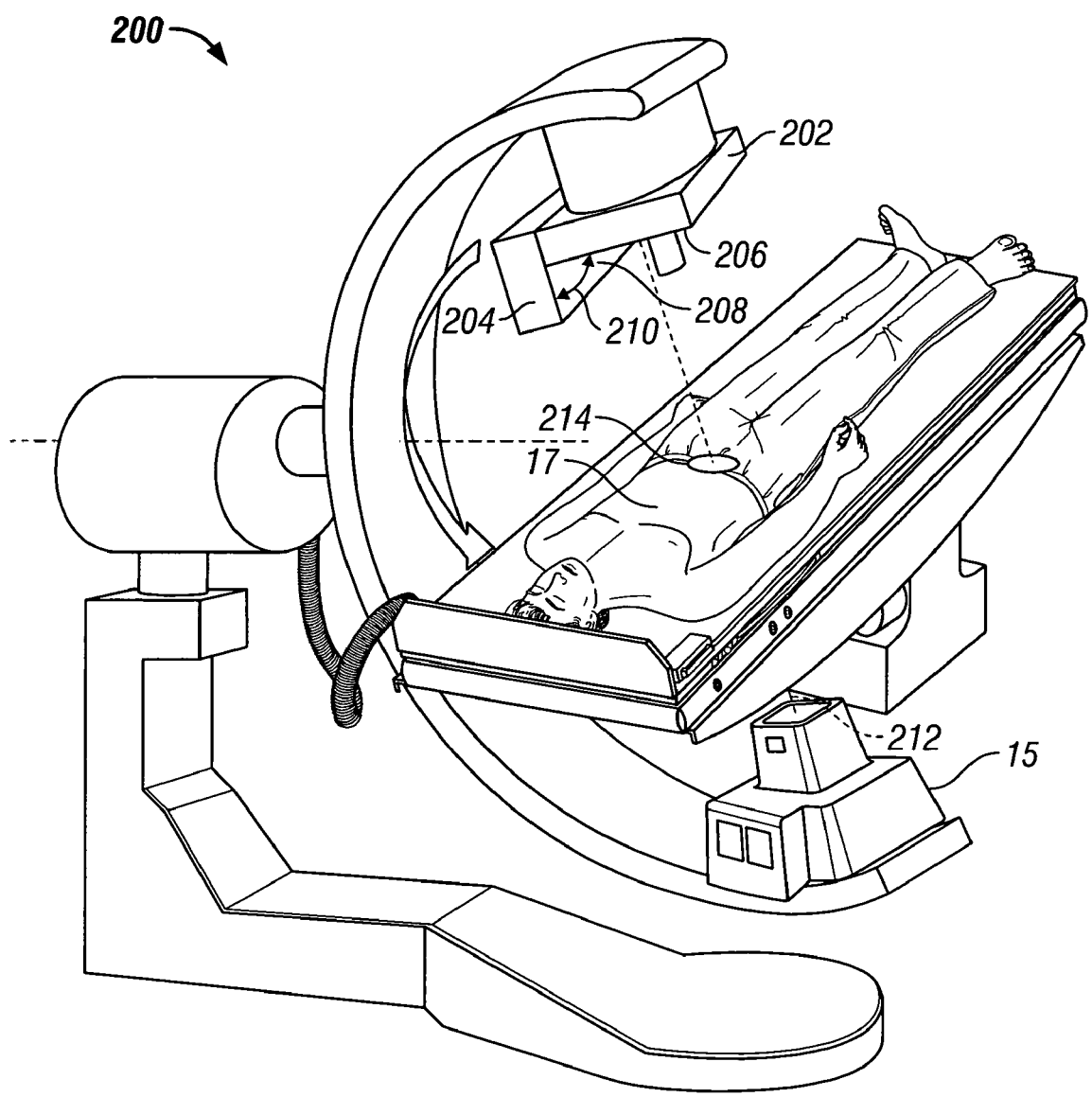
FIG. 2 is a schematic illustration of an imaging system in accordance with an another embodiment of the present invention.

FIG. 2 is a schematic illustration of an imaging system 200 in accordance with another embodiment of the present invention. Imaging system 200 is substantially similar to imaging system 10 (shown in FIG. 1) and components of imaging system 200 that are identical to components of imaging system 10 are identified in FIG. 2 using the same reference numerals used in FIG. 1. Accordingly, imaging system 200 includes a pair of dual x-ray/gamma ray detectors 202 and 204. In the exemplary embodiment, dual x-ray/gamma ray detectors 202 and 204 are configured to be interchangeable with dual x-ray/gamma ray detector 16 (shown in FIG. 1) by using similar connecting hardware through which dual x-ray/gamma ray detectors 202 and 204 and dual x-ray/gamma ray detector 16 are coupled to C-arm 14.

The detection fields 206 and 208 of detectors 202 and 204, respectively, are at an angle 210 relative to each other. In the exemplary embodiment, detectors 202 and 204 are spaced apart from each other. In an alternative embodiment, detectors 202 and 204 are in contact with each other.

In the exemplary embodiment, detectors 202 and 204 are arranged such that angle 210 is substantially 90 degrees with respect to each other. In an alternative embodiment, detectors 202 and 204 may be arranged at a plurality of selectable values of angle 210. Detectors 202 and 204 are configured such that detection field 208 is substantially perpendicular to an axis between detector 202 and x-ray source 15. In such a configuration, detector 202 may be used to detect transmission x-ray photons from x-ray source 15 and emission gamma photons from a radiopharmecuetical concentrated in a region of interest 214 within object 17. In the exemplary embodiment, detector 202 comprises CZT making it sensitive to and capable of discriminating between transmission x-ray photons and emission gamma photons. Accordingly, detector 202 may be used during a multi-modality scan wherein a portion of the scan is used to detect transmission x-rays from x-ray source 15 and a portion of the scan is used to detect emission gamma photons from the radiopharmecuetical within object 17.

Detector 204 is inclined with respect to detector 202 to facilitate cardiac scans, for example, to reduce a scan time of a SPECT scan of heart 62. Accordingly, detectors 202 and 204 may be used cooperatively to perform a SPECT scan of heart 62 for ninety degrees of rotation of C-arm 14 to effectively acquire a full one hundred and eighty degrees of SPECT data. The scan may continue for an additional ninety degrees plus a number of degrees of fan of beam 36 (shown in FIG. 1) to complete a full one hundred and eighty degrees of CT scan data. In this way, a SPECT scan may be completed in approximately one half the time of a SPECT scan acquired with only a single detector 202. Additionally, heart monitor 64 (shown in FIG. 1) may be used to synchronize transmission and/or emission photon image data during a scan.

During a multi-modality scan a CT portion of the scan may be performed at a relatively slow rate relative to and during a simultaneous SPECT image data acquisition. Moreover, CT and SPECT image data acquisition may be interleaved such that the SPECT portion of the scan is performed continuously and the CT portion of the scan is started and stopped to facilitate reducing acquisition of redundant CT image data. Starting and stopping the CT image data acquisition during a simultaneous CT and SPECT scan portion may further facilitate reducing an exposure of x-rays to object 17. A CT portion of the scan may also be performed at a relatively fast rate either before or after performing a SPECT portion of the scan.

During a multi-modality scan, with cardiac gating, a SPECT portion of a scan may be performed and then a CT portion of the scan may be performed by stepping C-arm 14 to a position corresponding to a next view in the scan. C-arm 14 may be held in a stationary position for a period of time to allow system 10 to be triggered by heart monitor 64 in response to a cardiac cycle of heart 62. A cycle for heart function that triggers system 10 may be selected by a user and may be adaptively configured to determine a trigger point during an abnormally periodic heart rate cycle. For example, heart monitor 64 may be selectably configured to generate a trigger during a systolic period or a diastolic period of the cardiac cycle. System 10 then may be programmed to reconstruct separate series of images per each selected heart cycle, thus obtaining 3-D CT images of heart 62 in each selected cycle period.

Further, system 10 may be programmed to compute an ejection fraction (EF), CT cine, visualize calcifications and fuse rendered NM and CT to correlate perfusion, viability and anatomy data. Cine scanning is used so that imaging is performed continuously for a selected period of time without moving table top 18 or C-arm 14. Each cine scan is made sufficiently long to ensure that a complete cardiac cycle of heart 62 is included. For example, in a cine scan of approximately two seconds, image data representative of a sequence of approximately forty four images may be obtained. Each image is approximately 0.1 second apart from the next and includes at least one complete cardiac cycle. Additional two-second cine scans may be performed. Patient table top 18 may be stepped between each two-second cine scan so that image slices from a subsequent scan do not overlap a volume imaged in slices from previous scans. In one embodiment, patient table top 18 is stepped an amount equal to a total thickness of the image slices acquired, to obtain a set of slices adjacent to, but not overlapping slices obtained prior to each step.

The combined transmission photon imaging and emission photon imaging modalities may also facilitate attenuation correction and localization. CT image data may be used as a-priori information for optimization of SPECT image reconstruction, fluoroscopy with NM, interventional (with or without navigation guidance) with CT/fluoro fused images, sentinel nodes excision, guided biopsy, and to facilitate correlating perfusion and viability data with angiography and calcium scoring.

FIG. 3 is a flowchart of an exemplary method 300 that may be used to perform a multi-modality image scan of an object using the imaging system. Method 300 includes aligning 302 a patient table in an opening of a C-arm unit that includes a CZT photon detector positioned, for example, at a first end of the C-arm and an x-ray source positioned, for example, at a second opposing end of the C-arm. The x-ray source is positioned such that a conical beam of x-ray photons, generated within the x-ray source, is directed diametrically across the C-arm unit towards the CZT photon detector through a portion of the patient table. Typically, the patient table supports a patient, lying supine upon the patient table. The CZT detector receives a portion of the generated x-rays and converts an interaction of the detector and x-rays into signals representative of structures within the patient. Moreover, the patient may have been administered a radiopharmecuetical that tends to concentrate in a volume of interest in the patient. The radiopharmecuetical emits gamma photons, a portion of which are directed towards the CZT detector. The CZT detector receives a portion of the emitted gamma photons and converts an interaction of the CZT detector and the gamma photons into signals representative of physiological processes occurring within the patient. The table is aligned such that a scan of the patient using the x-ray source and the CZT detector in conjunction with the gamma photons emitted from the volume of interest within the patient may be performed. Such a scan may include a transmission x-ray image acquisition portion and an emission gamma image acquisition portion. The portions may occur simultaneously, sequentially and/or the portions may be interleaved such that the emission gamma image acquisition portion of the scan may be started before the transmission x-ray image acquisition portion of the scan has completed, and the transmission x-ray image acquisition portion may be resumed prior to the completion of the emission gamma image acquisition portion of the scan.

Method 300 further includes imaging 304 a patient utilizing a first imaging modality during a first portion of a scan. The first modality may be, for example, a CT imaging modality that utilizes the x-ray source and the CZT detector along with a high count rate capable electronic processor. Method 300 also includes imaging 306 a patient utilizing a second imaging modality during a second portion of the scan. The scanned modality may be a nuclear medicine modality, such as, for example, SPECT. The SPECT modality may use a single detector such as the CZT detector that is used for the CT portion of the scan, but the imaging system may also be configured to utilize a pair of SPECT detectors inclined at an angle with respect to each other. Such a configuration may facilitate reducing a scan time for a SPECT scan in that the detectors may cooperate to acquire an amount of data for a one hundred and eighty degree scan in only ninety degrees of rotation of the detectors. During a scan, acquisition of images using either or both modalities may be facilitated by synchronizing the image acquisition with a heart monitor that may trigger the image acquisition or may tag the image data such that a reconstructed series of images may only includes images from a selected portion of a cardiac or other physiological cycle.

It is contemplated that the benefits of the invention accrue to all multi-modality imaging systems, such as, for example, but not limited to, a CT/SPECT imaging system.

The above-described multi-modality imaging systems provide a cost-effective and reliable means for examining a patient. For example, the imaging system includes a cone-beam CT imaging modality that facilitates utilization of an entire surface area of a CZT imaging detector. For example, nuclear medicine scans are volume scans, which are well suited for a plane detector. Typically, CT x-ray sources emit a fan-beam of x-rays that are directed to a linearly arrayed detector such that a slice of an object is imaged in each view. To accommodate the plane detector used with a nuclear medicine modality, a cone-beam CT x-ray source may be used to take advantage of the additional detector surface area afforded by the plane detector configuration. As a result, an imaging system is provided that permits multi-modality imaging using an entire surface area of the CZT detector during each modality of the scan.

Exemplary embodiments of a multi-modality imaging system are described above in detail. The multi-modality imaging system components illustrated are not limited to the specific embodiments described herein, but rather, components of each multi-modality imaging system may be utilized independently and separately from other components described herein. For example, the multi-modality imaging system components described above may also be used in combination with other imaging systems.

While the invention has been described in terms of various specific embodiments, those skilled in the art will recognize that the invention can be practiced with modification within the spirit and scope of the claims.

What is claimed is:

1. A method of examining a patient, the method comprising:

aligning a patient table in an opening of a gantry of a C-arm unit that includes a CZT photon detector and an x-ray source;

imaging a patient utilizing a first imaging modality during a first portion of a scan using the CZT detector;

imaging the patient utilizing a second imaging modality during a second portion of the scan using the CZT detector wherein the second imaging modality is different than the first imaging modality; and imaging the patient utilizing the first imaging modality during a third portion of the scan using the CZT detector.

2. A method in accordance with claim 1 further comprising moving the patient table along at least one of a patient table orthogonal axis when imaging the patient utilizing at least one of the first imaging modality and the second imaging modality.

3. A method in accordance with claim 1 further comprising rotating the gantry around a longitudinal axis of the patient table when imaging the patient utilizing at least one of the first imaging modality and the second imaging modality.

4. A method in accordance with claim 3 wherein the x-ray source is configured to emit x-rays in a beam having a predetermined fan angle, said method further comprising rotating the gantry around a longitudinal axis of the patient table less than one hundred and eighty degrees of rotation when imaging the patient utilizing at least one of the first imaging modality and the second imaging modality.

5. A method in accordance with claim 3 wherein the x-ray source is configured to emit x-rays in a beam having a predetermined fan angle, said method further comprising rotating the gantry around a longitudinal axis of the patient table approximately one hundred and eighty degrees plus the fan angle of rotation when imaging the patient utilizing at least one of the first imaging modality and the second imaging modality.

6. A method in accordance with claim 1 further comprising moving at least one of the CZT photon detector and the patient table to follow a contour of the patient during at least a portion of a scan.

7. A method in accordance with claim 1 wherein the patient includes a radiopharmecuetical and wherein imaging the patient utilizing a first imaging modality comprises imaging the patient using a nuclear medicine modality.

8. A method in accordance with claim 7 wherein imaging the patient using a nuclear medicine modality comprises imaging the patient using single positron emission computed tomography (SPECT).

9. A method in accordance with claim 8 wherein imaging the patient using a nuclear medicine modality comprises imaging the patient using a pair of photon detectors using a SPECT modality.

10. A method in accordance with claim 1 wherein imaging a patient utilizing a first imaging modality comprises imaging the patient using a computer tomography (CT) modality.

11. A method in accordance with claim 10 wherein imaging the patient using a CT modality comprises imaging the patient using a cone-beam CT modality.

12. A method in accordance with claim 1 further comprising:

monitoring a cyclic physiological function within the patient; and triggering at least one of the first modality and the second modality during at least one preselected portion of the cyclical physiological function.

13. An imaging system comprising a gantry unit having an x-ray source for generating x-rays and a CZT detector configured to detect emission gamma photons and transmission x-ray photons, and a C-arm configured to move the x-ray source and detector along an image acquisition path between at least first and second imaging positions defining a plurality of alternating scan portions that utilize different imaging modalities.

14. An imaging system in accordance with claim 13 wherein said gantry is at least one of rotatably coupled to a gantry holder and slidably coupled to the gantry holder.

15. An imaging system in accordance with claim 14 wherein said x-ray source is configured to emit x-rays in a beam having a predetermined fan angle and wherein said gantry is configured to slidably translate along said gantry holder an angular distance of approximately one hundred eighty degrees plus the fan angle of the x-ray source.

16. An imaging system in accordance with claim 13 wherein said x-ray source comprises a cone-beam x-ray source.

17. An imaging system in accordance with claim 13 wherein said detector comprises a pair of detectors inclined at an angle with respect to each other.

18. An imaging system in accordance with claim 17 wherein said detector comprises a pair of detectors inclined at an angle of approximately ninety degrees with respect to each other.

19. An imaging system in accordance with claim 17 wherein at least one of said pair of detectors comprises cadmium zinc telluride (CZT).

20. An imaging system in accordance with claim 17 wherein at least one of said pair of detectors is positioned substantially perpendicularly opposed to said x-ray source.

21. An imaging system in accordance with claim 20 wherein said at least one of said pair of detectors that is positioned substantially perpendicularly opposed to said x-ray source comprises CZT.

22. An imaging system in accordance with claim 13 further comprising a patient table configured to translate along at least one of three axes.

23. An imaging system in accordance with claim 22 wherein said system is configured to control at least one of the patient table and the gantry to cause the detector to follow a contour of an object to be scanned.

24. An imaging system in accordance with claim 13 including an imaging isocentric area located between said x-ray source and said detector, said imaging isocentric area remaining substantially constant when said gantry moves along said image acquisition path.

25. An imaging system in accordance with claim 13 wherein said imaging system comprises a gantry support base wherein said support base is coupled to a rail system, said rail system operable to move said gantry unit along at least one axes.

26. An imaging system in accordance with claim 25 wherein said rail system is coupled to at least one of a floor, a ceiling, and a wall of an examination room.

27. An imaging system in accordance with claim 13 wherein said imaging system comprises a gantry support base wherein said gantry support base is a mobile support base.

* * * * *